United States Patent [19]

Kawashima et al.

[11] Patent Number: 4,756,303
[45] Date of Patent: Jul. 12, 1988

[54] INSERTION SECTION OF AN ENDOSCOPE

[75] Inventors: Masahiro Kawashima; Koji Kambara; Tsuruo Hatori; Nobuaki Akui; Nobuhiko Washizuka; Kunio Ohno; Yoshio Tashiro, all of Tokyo, Japan

[73] Assignee: Olympus Optical Co., Ltd., Japan

[21] Appl. No.: 911,768

[22] Filed: Sep. 26, 1986

[30] Foreign Application Priority Data

Sep. 30, 1985 [JP] Japan ................................ 60-216679
Aug. 8, 1986 [JP] Japan ................................ 60-186509

[51] Int. Cl.$^4$ ................................................ A61B 1/06
[52] U.S. Cl. ................................................ 128/6
[58] Field of Search ........................... 128/3, 4, 5, 6, 7

[56] References Cited

U.S. PATENT DOCUMENTS 4,146,019 3/1979 Bass et al. ............................... 128/6
4,567,882 2/1986 Heller ..................................... 128/6
4,587,972 5/1986 Morantte, Jr. ....................... 128/4 X Primary Examiner—William H. Grieb

[57] ABSTRACT

In an insertion section of an endoscope according to the present invention, a plurality of flexible segment tubes, each having a predetermined length and a predetermined inside diameter, constitute necessary ducts for the endoscope, individually. The ducts include an image guide duct, light guide duct, instrument channel duct, and air/water channel duct. The flexible segment tubes are fixed in a housing tube. In manufacturing the insertion section, optical fibers and the like are inserted into the flexible tubes, fixed in the housing tube. Once the housing tube is molded, the respective sectional configurations of the flexible tubes are kept uniform, even though the housing tube may contract. Thus, the optical fibers and other elements can be inserted easily into the ducts.

19 Claims, 8 Drawing Sheets

INSERTION SECTION OF AN ENDOSCOPE

BACKGROUND OF THE INVENTION

The present invention relates to an endoscope using a multi-lumen tube in an insertion section.

An endoscope of this type is disclosed in U.S. Pat. No. 4,576,145. An insertion section of this endoscope includes an elongated multi-lumen tube, formed of a flexible resin. The multi-lumen tube contains a plurality of conduits, each having a predetermined inside diameter and extending in the axial direction of the tube. Some of the conduits are used as an image guide duct or light guide duct, in which optical fibers, lenses, etc., are inserted. The other conduits serve as an air/water channel duct for air or water supply, or an instrument channel duct in which a medical instrument is inserted.

As stated in Japanese Utility Model Disclosure No. 55-171001, however, the multi-lumen tube is molded by extrusion. After it is molded therefore, the tube may possibly contract, thereby reducing the diameters of the conduits or changing their sectional configurations. Thus, it sometimes is very difficult to insert the optical fibers and lenses into the conduits, after the multi-lumen tube is formed on the conduits.

Moreover, pipes, extending from an operating section of the endoscope, are inserted individually into the instrument and air/water channel ducts, so that the conduits and their corresponding pipes are connected. The respective sectional configurations of the pipes are usually uniform, while those of the conduits are different. Accordingly, the pipes cannot be inserted properly into the conduits, thus entailing defective connection.

SUMMARY OF THE INVENTION

The object of the present invention is to provide an endoscope, in which a multi-lumen tube is used in an insertion section, and in which the respective sectional configurations of ducts are uniform, so that optical fibers and lenses can be inserted easily into some of the ducts, such as an image guide duct, and that pipes, extending from an operating section, are connected properly to the other ducts, such as an air/water channel duct.

In an insertion section of an endoscope according to the present invention, a plurality of flexible segment tubes, each having a predetermined length and a predetermined inside diameter, constitute ducts for the endoscope, individually. The ducts include an image guide duct, light guide duct, instrument channel duct, and air/water channel duct. The flexible segment tubes are fixed in a housing tube. In manufacturing the insertion section, optical fibers and the like are inserted into the flexible tubes, fixed in the housing tube. Once the housing tube is molded, the respective sectional configurations of the flexible tubes are kept uniform, even though the housing tube may contract. Thus, the optical fibers and other elements can be inserted easily into the ducts.

DETAILED DESCRIPTION OF THE PREFERRED EMBODIMENTS

Figure 1:
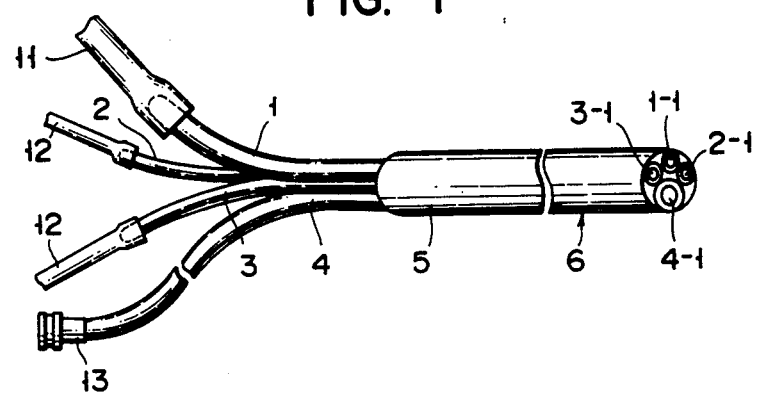
FIG. 1 is a perspective view of an insertion section of an endoscope according to a first embodiment of the present invention.
Figure 2:
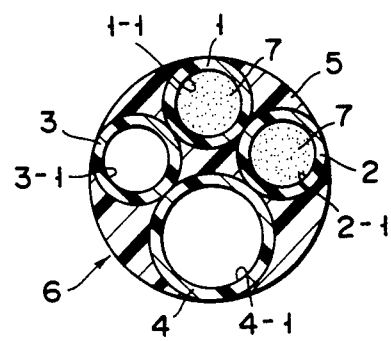
FIG. 2 is a sectional view of the insertion section of the endoscope shown in FIG. 1.

FIGS. 1 and 2 show a first embodiment of the present invention. As shown in FIG. 1, insertion section 6 of an endoscope includes flexible segment tubes 1, 2, 3 and 4 and housing tube 5. The four flexible segment tubes, each having a predetermined length and a predetermined inside diameter, are formed of a flexible resin. Tubes 1 to 4 are covered by tube 5, which is formed of a flexible resin, as mentioned later.

Flexible segment tubes 1 and 2 serve as image guide duct 1-1 and light guide duct 2-1, respectively, in which optical fibers 7 and lenses are inserted. Tube 3 is used as air/water channel duct 3-1, through which air, water, or the like flows. Tube 4 is used as instrument channel duct 4-1 to receive a medical instrument. Those ends of tubes 1 to 3 on the side of an operating section (not shown) are inserted individually in tubes 11 and 12, for connection. Since the tubes and their corresponding tubes 11 and 12 have uniform cross-sectional configurations, joint portions between them are kept watertight. Tube 4 is provided, on its end on the operating-section side, with mouthpiece 13 which is to be connected to a tube, extending from the operating section.

Figure 3:
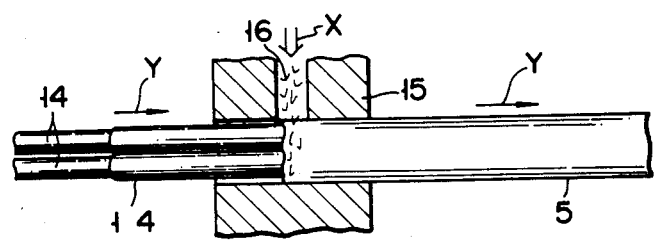
FIG. 3 is a sectional view schematically showing an apparatus for manufacturing the insertion section of FIG. 1.

The insertion section of the endoscope, with the aforementioned construction, is fabricated on a manufacturing apparatus, as shown in FIG. 3. Tubes 1 to 4 are bundled in parallel relation, and cores 14, having a diameter equal to the inside diameter of the tubes, are inserted individually into the tubes. In this state, tubes 1 to 4 are set in an opening of molding die 15. While molten resin is being fed in the direction of a arrow X, from molten-resin passage 16 onto tubes 1 to 4, the tubes are pulled in the direction of arrow Y, and drawn out of the opening of die 15. As a result, tubes 1 to 4 are coated with the resin, and at the same time, the gaps between the tubes are filled up with the resin. Thus, housing tube 5, covering flexible segment tubes 1 to 4, is formed. After tube 5 solidifies, cores 14 are drawn out of tubes 1 to 4. In this manner, insertion section 6 of the endoscope is completed, in which tubes 1 to 4, constituting image guide duct 1-1, light guide duct 2-1, and channel ducts 3-1 and 4-1, respectively, are inserted in housing tube 5. Thereafter, optical fibers 7 and the like are inserted into tubes 1 to 4, fixed in tube 5. In this case, even if tube 5 contracts after it is formed, the sectional configurations of tubes 1 to 4 will be kept uniform. Thus, fibers 7 and other elements can be inserted easily into the ducts.

Figure 4:
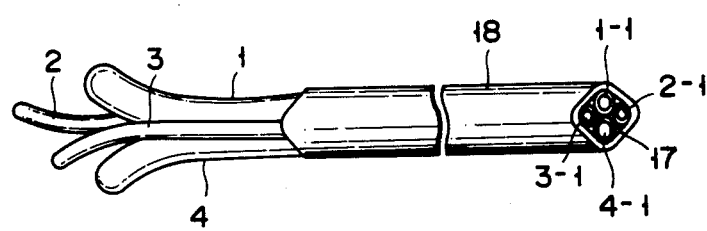
FIG. 4 is a perspective view of an insertion section of an endoscope according to a second embodiment of the invention.
Figure 5:
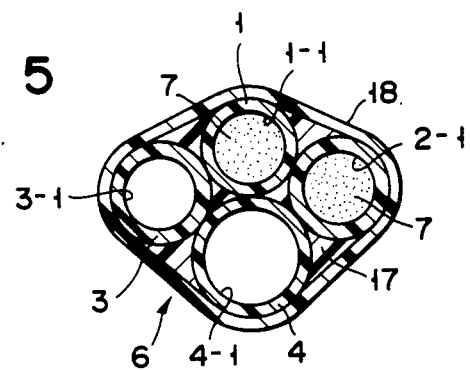
FIG. 5 is a sectional view of the insertion section of the endoscope shown in FIG. 4.
Figure 6:
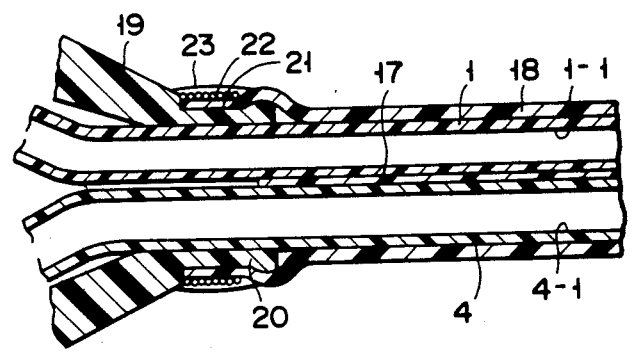
FIG. 6 is a sectional view of a connecting portion between the insertion section and an operating section of the endoscope shown in FIG. 4.

FIGS. 4, 5 and 6 show a second embodiment of the invention. Insertion section 6 of an endoscope, according to the second embodiment, is manufactured as follows. In this embodiment, housing tube 5 is formed of flexible resin 17 and heat-contractile tube 18. As in the first embodiment, cores 14, having a diameter equal to the inside diameter of flexible segment tubes 1 to 4, are inserted individually into tubes 1 to 4. The flexible tubes are bundled in parallel relation. The gaps between tubes 1 to 4, in this state, are filled up with flexible resin 17, and contractile tube 18 is fitted on tubes 1 to 4. Then, tube 18 is heated and contracted. Thereafter, cores 14 are drawn out of tubes 1 to 4. In the second embodiment, tubes 1 to 4 are fitted in housing tube 5 by the contractile force of tube 18.

As shown in FIG. 6, an operating section (not shown) and insertion section 6 are connected in the following manner. Annular groove 21 is formed on end portion 20 of pipe 19, which extends from the operating section. That end portion of heat-contractile tube 18 on the operating-section side, covers end portion 20 of pipe 19. In this state, if tube 18 is heated and contracted, the same end portion of tube 18 is brought closely into contact with end portion 20 of pipe 19. It is wound with combined thread 22, such as nylon gut, silk thread, cotton thread, etc., and epoxy-based bonding agent 23 is applied to thread 22. As a result, pipe 19 and tube 18 are connected closely, so that the inside of the operating section is kept watertight.

Figure 7:
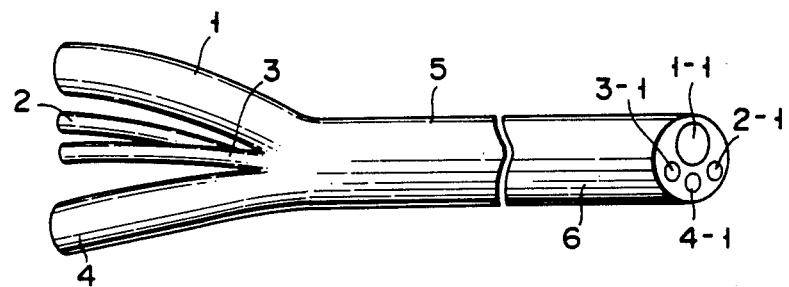
FIG. 7 is a perspective view of an insertion section of an endoscope according to a third embodiment of the invention.
Figure 8:
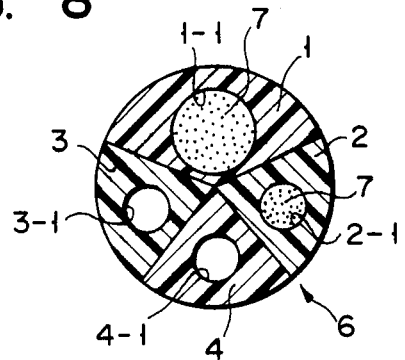
FIG. 8 is a sectional view of the insertion section of the endoscope shown in FIG. 7.
Figure 9:
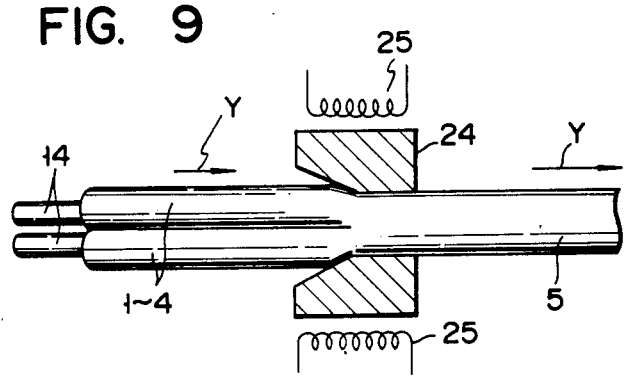
FIG. 9 is a sectional view schematically showing an apparatus for manufacturing the insertion section of FIG. 7.

FIGS. 7, 8 and 9 show a third embodiment of the invention. Insertion section 6 of an endoscope, according to the third embodiment, is composed of thick-walled flexible segment tubes 1 to 4 which are thermally bonded to each other. The insertion section is not provided with such a housing tube as shown in FIG. 2. More specifically, insertion section 6 of the endoscope of this embodiment is manufactured in the following manner, by means of a manufacturing apparatus shown in FIG. 9. Cores 14, having a diameter equal to the inside diameter of flexible segment tubes 1 to 4, are inserted individually into tubes 1 to 4. The flexible segment tubes are bundled in parallel relation. In this state, tubes 1 to 4 are set in an opening of molding die 24. Heaters 25, attached to die 24, heat tubes 1 to 4 until the tubes melt. Then, tubes 1 to 4 are pulled in the direction of arrow Y, and drawn out of the opening of die 24. At the same time, tubes 1 to 4 are fixedly bonded to each other. After flexible segment tubes 1 to 4 solidify, cores 14 are drawn out of tubes 1 to 4. In this manner, insertion section 6 of the endoscope is completed, in which tubes 1 to 4, constituting image guide duct 1-1, light guide duct 2-1, and channel ducts 3-1 and 4-1, respectively.

Figure 10:
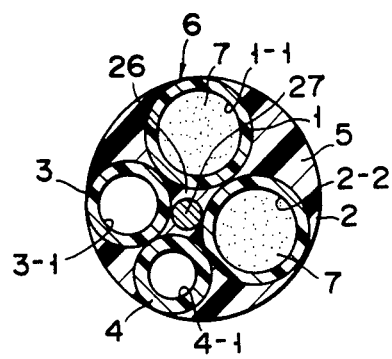
FIG. 10 is a sectional view of an insertion section of an endoscope according to a fourth embodiment of the invention.

FIG. 10 shows a fourth embodiment of the invention. In this embodiment, wire 27 is passed through insertion section 6 of an endoscope, constructed in the same manner as in the first embodiment. Flexible segment tubes 1 and 2 serve as image guide duct 1-1 and light guide duct 2-1, respectively, in which optical fibers 7 and lenses are inserted. Tube 3 is used as air/water channel duct 3-1, through which air, water, or the like flows. Tube 4 is used as instrument channel duct 4-1 to receive a medical instrument. Housing tube 5 covers tubes 1 to 4. Wire 27 is passed through inside space 26 of tube 5. Thus, if insertion section 6 is pulled in its axial direction, wire 27 never stretches, so that section 6 cannot stretch axially. Accordingly, optical fibers 7 cannot be broken by stretching axially. Since wire 27 is passed through a dead space in tube 5, the use of it in tube 5 does not require the diameter of insertion section to be increased.

Figure 11:
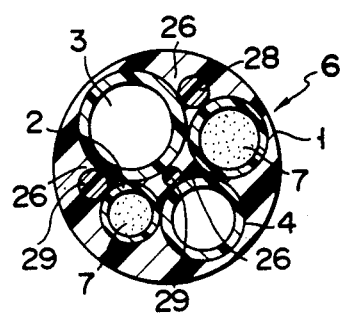
FIG. 11 is a sectional view of an insertion section of an endoscope according to a fifth embodiment of the invention.

FIG. 11 shows a fifth embodiment of the invention. In this embodiment, laser probe 28 and a pair of measurement fibers 29, instead of wire 27 of the fourth embodiment, are passed through inside space 26 of housing tube 5. Thus, with use of an endoscope having insertion section 6 according to the fifth embodiment, laser treatment of the affected part and measurement of pressure inside the body cavity, can be effected.

Figure 12:
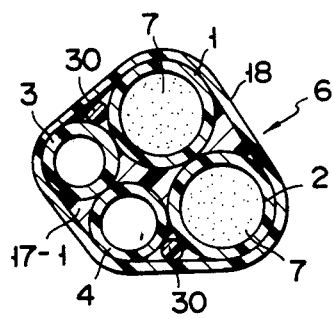
FIG. 12 is a sectional view of an insertion section of an endoscope according to a sixth embodiment of the invention.

FIG. 12 shows a sixth embodiment of the invention. In this embodiment, wire 30 is passed through insertion section 6, constructed in the same manner as in the second embodiment. Housing tube 5 includes resin portion 17-1 filled in gaps between flexible tubes 1 to 4, and heat-contractile tube 18 covering tubes 1 to 4. A pair of wires 30 are passed through resin portion 17-1, in symmetrical relation. Thus, wires 30 function in the same manner as wire 27 of the fourth embodiment. They also serve as operating wires for bending insertion section.

Figure 13:
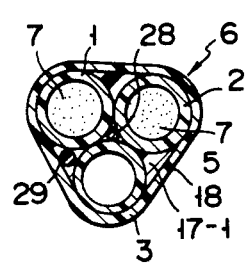
FIG. 13 is a sectional view of an insertion section of an endoscope according to a seventh embodiment of the invention.

FIG. 13 shows a seventh embodiment of the invention. In this embodiment, laser probe 28 and measurement fiber 29, instead of wires 30 of the sixth embodiment, are passed through resin portion 17-1 of houwing tube 5.

Figure 14:
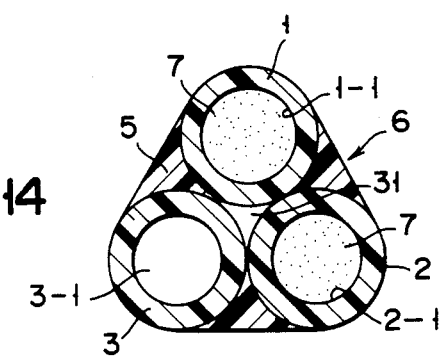
FIG. 14 is a sectional view of an insertion section of an endoscope according to an eighth embodiment of the invention.
Figure 15:
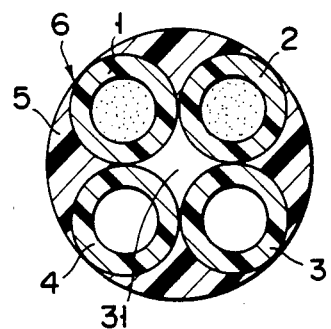
FIG. 15 is a sectional view of an insertion section of an endoscope according to a ninth embodiment of the invention.
Figure 16:
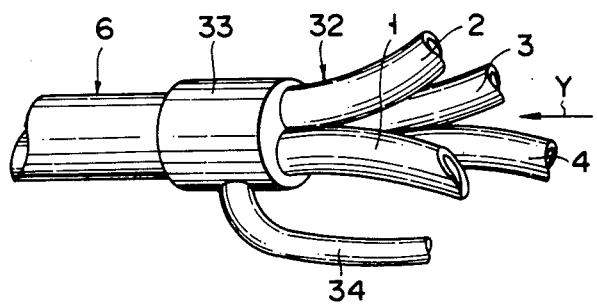
FIG. 16 is a perspective view of a connecting portion between the insertion section and an operating section of the endoscope shown in FIG. 15.
Figure 17:
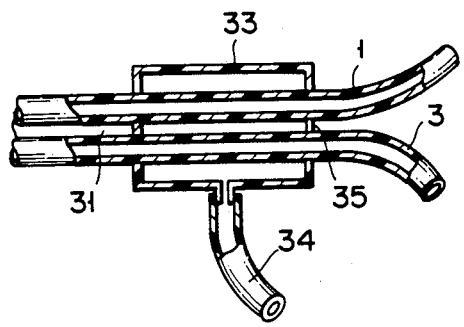
FIG. 17 is a sectional view of the connecting portion shown in FIG. 16.
Figure 18:
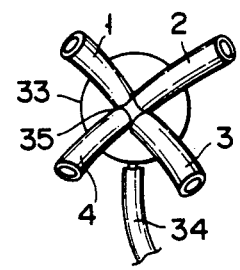
FIG. 18 is a perspective view of the connecting portion taken in the direction of arrow Y of FIG. 16.

FIG. 14 shows an eighth embodiment of the invention. In this embodiment, three flexible tubes 1, 2 and 3 are bundled parallel to and in close contact with one another. Housing tube 5 confines tubes 1 to 3, in this state. Tubes 1 and 2 serve as image guide duct 1-1 and light guide duct 2-1, respectively. Tube 3 is used as instrument channel duct 3-1. A space surrounded by tubes 1 to 3 constitutes sub-channel 31, which is used as an air/water channel duct.

FIGS. 15 to 18 shows a ninth embodiment of the invention. In this embodiment, four flexible segment tubes 1, 2, 3 and 4 are bundled parallel to and in close contact with one another. Housing tube 5 covers tubes 1 to 4, in this state. As in the eighth embodiment, a space surrounded by tubes 1 to 4 constitutes sub-channel 31. Cylindrical member 33 is attached to end portion 32 of insertion section 6 on the side of an operating section. Pipe 34, extending from the operating section, is connected to the peripheral wall of member 33. Thus, sub-channel 31 communicates with pipe 34 through member 33, and is used as an air/water channel duct. Sealing member 35, such as a bonding agent, closes the operating-section side end of sub-channel 31.

Figure 19:
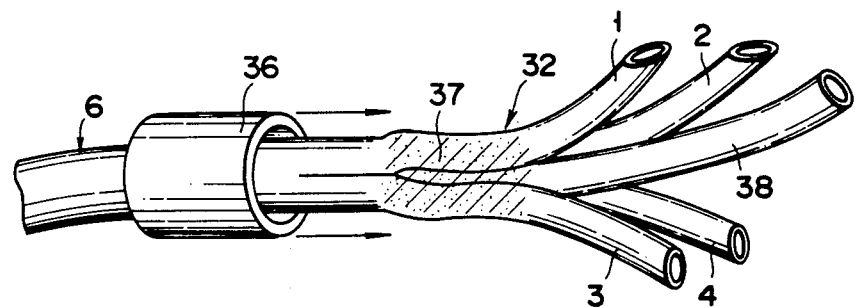
FIGS. 19 and 20 are perspective views of a connecting portion between an insertion section and an operating section of an endoscope according to a tenth embodiment of the invention, illustrating processes for manufacturing a diverging portion of the endoscope.
Figure 20:
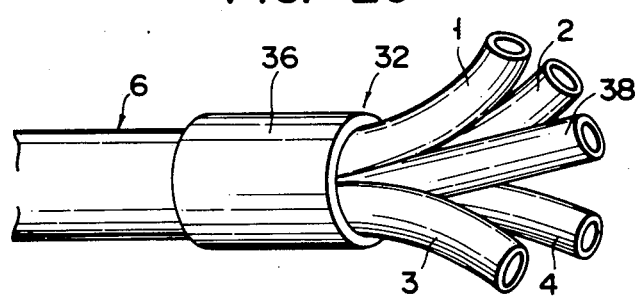
Figure 21:
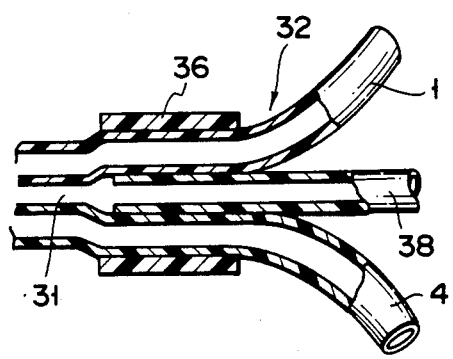
FIG. 21 is a sectional view of a connecting portion of the endoscope shown in FIG. 20.

FIGS. 19 to 21 show a tenth embodiment of the invention. In this embodiment, ring 36, instead of cylindrical member 33 of the ninth embodiment, is attached to end portion 32 of insertion section 6 on the side of an operating section. Flexible segment tubes 1, 2, 3 and 4 diverge from portion 32. A bonding agent is applied to fork portion 37, and ring 36 is fitted on portion 37. Pipe 38, extending from the operating section, is inserted in the end portion of sub-channel 31. Thus, sub-channel 31 serves as an air/water channel duct.

Figure 22:
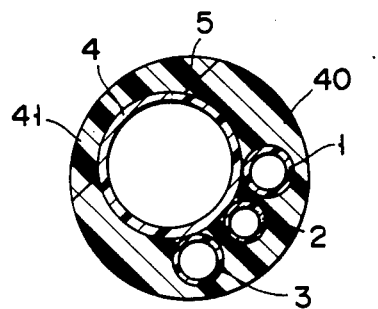
FIG. 22 is a sectional view of an insertion section of an endoscope according to an eleventh embodiment of the invention.

FIG. 22 shows an eleventh embodiment of the invention. In this embodiment, there are arranged small-diameter flexible segment tubes 1, 2 and 3 and large-diameter flexible segment tube 4. Housing tube 5 covers tubes 1 to 4. In this case, tubes 1 to 4 have different diameters, so that the wall thickness of tube 5 is uneven. More specifically, tube 5 includes thick-walled portion 40, formed of a soft resin, and thin-walled portion 41, formed of a rigid resin. Thus, the flexibility of tube 5 is uniform, with respect to every direction on its cross section.

Figure 23:
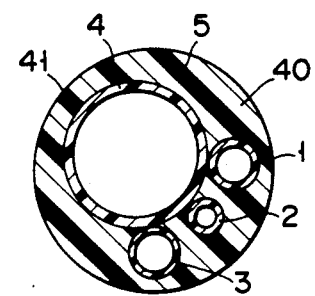
FIG. 23 is a sectional view of an insertion section of an endoscope according to a twelfth embodiment of the invention.
Figure 24:
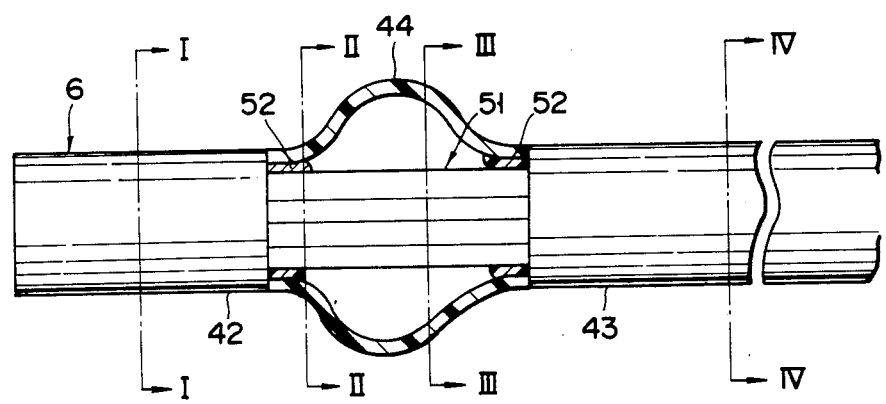
FIG. 24 is a cutaway side view of an insertion section of an endoscope according to a thirteenth embodiment of the invention.
Figure 25:
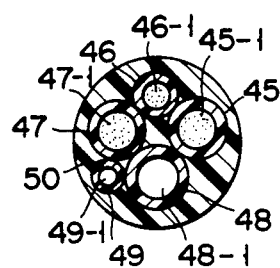
FIG. 25 is a sectional view taken along line I—I of FIG. 24.
Figure 26:
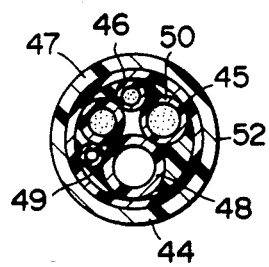
FIG. 26 is a sectional view taken along line II—II of FIG. 24.
Figure 27:
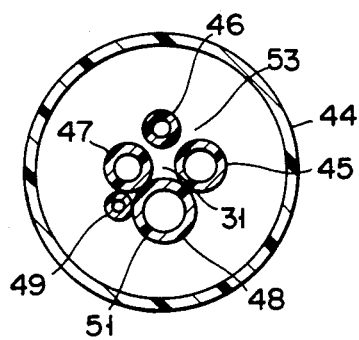
FIG. 27 is a sectional view taken along line III—III of FIG. 24.
Figure 28:
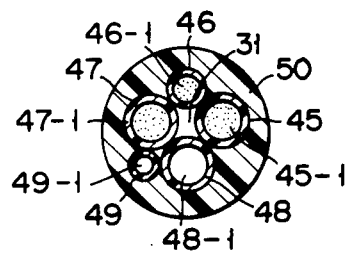
FIG. 28 is a sectional view taken along line IV—IV of FIG. 24.

FIG. 23 shows a twelfth embodiment of the invention. In this embodiment, as in the eleventh embodiment, there are arranged small-diameter flexible segment tubes 1, 2 and 3 and large-diameter flexible segment tube 4. Tubes 1 to 3 are formed of a soft resin, while tube 4 is made of a rigid resin. Housing tube 5 covers tubes 1 to 4. In tube 5, whose flexibility should otherwise be uneven, flexible tube 4 of the rigid resin is disposed at thin-walled portion 41, while flexible segment tubes 1 to 3 of the soft resin are arranged at thick-walled portion 40. Thus, the flexibility of tube 5 is uniform, with respect to every direction on its cross section.

FIGS. 24 to 28 show a thirteenth embodiment of the invention. In this embodiment, balloon 44 is provided in the middle of insertion section 6. Housing tube 50 covers five flexible segment tubes 45, 46, 47, 48 and 49, which are bundled in close contact with one another. Tube 45 serves as image guide duct 45-1, while tubes 46 and 47 are used as light guide ducts 46-1 and 47-1, respectively. Also, tubes 48 and 49 are used as instrument channel duct 48-1 and air/water channel duct 49-1, respectively.

At the middle portion of insertion section 6, flexible segment tubes 45 to 49 are not covered by housing tube 5. Balloon 44, formed of an elastic tube, is provided at uncovered middle portion 51. Two opposite end openings of balloon 44 are bonded individually to distal-end side 42 and operating-section side 43 of tube 5, by means of bonding agent 52. At portion 51, exposed from tube 50, tube 46 is separated from tubes 45 and 47, with gap 53 between them. At operating-section side 43, a space surrounded by tubes 45 to 49 constitutes sub-channel 31. Thus, balloon 44 communicates with sub-channel 31 via gap 53. In this arrangement, balloon 44 inflates when supplied with air from the operating section, through sub-channel 31, and deflates when the supplied air is sucked out through the sub-channel.

What is claimed is:

1. An endoscope having an insertion section, said insertion section comprising:
   a plurality of flexible segment tubes formed of a flexible resin and individually constituting ducts, each said flexible segment tube having a predetermined length and a predetermined inside diameter; and
   a housing tube formed of a flexible resin and fixing said flexible segment tubes, said flexible segment tubes being fixed in place in said housing tube with their interstices filled in a resin of which said housing tube is made of as one unit.

2. An endoscope according to claim 1, wherein said ducts include an image guide duct, a light guide duct, an instrument channel duct, and an air/water channel duct.

3. An endoscope according to claim 1, further comprising a wire in said housing tube.

4. An endoscope according to claim 1, further comprising a laser probe in said housing tube.

5. An endoscope according to claim 1, further comprising a fiber for measurement in said housing tube.

6. An endoscope according to claim 1, wherein said plurality of flexible segment tubes are arranged in close contact with one another, so that a space surrounded by said flexible segment tubes constitutes a sub-channel.

7. An endoscope according to claim 6, further comprising a pipe connected to an end portion of the sub-channel.

8. An endoscope according to claim 7, further comprising a cylindrical member covering the end portion of the sub-channel and connected to the pipe.

9. An endoscope according to claim 1, wherein said housing tube includes a portion formed of a soft resin, and a portion formed of a rigid resin.

10. An endoscope according to claim 1, wherein said plurality of flexible segment tubes include flexible segment tubes formed of a soft resin, and flexible segment tubes formed of a rigid resin.

11. An endoscope according to claim 1, wherein said flexible segment tubes have a portion not covered by the housing tube, and which further comprise a balloon formed of an elastic tube and attached to the uncovered portion.

12. An endoscope having an insertion section, said insertion section comprising:
   a plurality of flexible segment tubes formed of a flexible resin and individually constituting ducts, each said flexible segment tube having a predetermined length and a predetermined inside diameter; and a housing tube formed of a flexible resin and fixing said flexible segment tubes, said housing tube being formed of a resin filled in gaps between said flexible segment tubes, and a heat-contractible tube covering the resin.

13. An endoscope according to claim 12, wherein said ducts include an image guide duct, a light guide duct, an instrument channel duct, and an air/water channel duct.

14. An endoscope according to claim 12, further comprising a wire in said housing tube.

15. An endoscope according to claim 12, further comprising a laser probe in said housing tube.

16. An endoscope according to claim 12, further comprising a fiber for measurement in said housing tube.

17. An endoscope according to claim 12, wherein said plurality of flexible segment tubes include flexible segment tubes formed of a soft resin, and flexible segment tubes formed of a rigid resin.

18. An endoscope having an insertion section which has an outer peripheral surface, said insertion section comprising:

a plurality of flexible segment tubes formed of a flexible resin and individually constituting ducts, each said flexible segment tube having a predetermined length, a predetermined inside diameter, and a surface which constitutes part of the outer peripheral surface of said insertion section, and thermally bonded to each other.

19. An endoscope according to claim 18, wherein said ducts include an image guide duct, a light guide duct, an instrument channel duct, and an air/water channel duct.

* * * * *